United States Patent [19]

Giacalone

[11] Patent Number: 4,588,397
[45] Date of Patent: May 13, 1986

[54] EXTERNAL CATHETER FOR INCONTINENT MALES

[76] Inventor: Joseph J. Giacalone, 2547 La Serena, Escondido, Calif. 92025

[21] Appl. No.: 739,696

[22] Filed: May 31, 1985

Related U.S. Application Data

[63] Continuation-in-part of Ser. No. 559,344, Dec. 8, 1983.

[51] Int. Cl.$^4$ .................................................. A61F 5/44
[52] U.S. Cl. ...................................... 604/349; 604/351
[58] Field of Search .................... 2/405; 285/260, 208, 285/DIG. 16; 604/346–353

[56] References Cited

U.S. PATENT DOCUMENTS

| | | | |
|---|---|---|---|
| 3,405,714 | 10/1968 | Moss | 604/350 |
| 3,526,227 | 1/1970 | Appelbaum | 604/350 |
| 3,721,243 | 3/1973 | Hesterman et al. | 604/353 |
| 3,999,550 | 12/1976 | Martin | 604/353 |

*Primary Examiner*—J. L. Kruter
*Attorney, Agent, or Firm*—Frank D. Gilliam

[57] ABSTRACT

An improved external catheter for incontinent males. The external catheter consists of three interrelated components. A generally tubular sheath having a fluid drainage tube connection at one end and a reinforcing ring at the other is adapted to fit over the penis with the ring at the base of the penis. A frusto-conical seal of elastic material having a reinforcing ring at the base end is adapted to fit within the sheath with the ring at the base of the penis adjacent to the sheath ring. The wall of the frustom extends along the penis in snug engagement therewith. A nether garment to be worn by the patient has a penis-receiving hole surrounded by a pair of collars separated by a flange. A first collar extends exterior of the garment and a second collar is positioned adjacent the base of the penis. Each collar has a circular channel means with the channel opening extending outwardly away from the penis. With all three components in place, the sheath ring is extended slightly and shaped into the first collar channel, and the reinforcing ring is extended and snapped into the second collar channel sealing the ring and sheath to the collar and using the nether garment to resist forces tending to remove the sheath and seal. This external catheter assembly is extremely resistant to seepage of urine or to bring forced off of the penis by a sudden large flow of urine.

7 Claims, 4 Drawing Figures

EXTERNAL CATHETER FOR INCONTINENT MALES

BACKGROUND OF THE INVENTION

This application is a continuation-in-part of my pending application having Ser. No. 559,344, filed on Dec. 8, 1983.

This invention relates in general to urine drainage systems for incontinent males and, more specifically, to an improved external catheter system having improved resistance to leakage.

With advanced age, disease, nerve damage or the like, people sometimes lose the ability to control the flow of urine. There may be a gradual leakage of urine with an occasional sudden heavy flow of urine.

Attempts have been made to drain the urine both with internal catheters extending into the urethra and with external catheters which (for males) includes a sheath surrounding the penis and connected to a drain line to convey urine to a receptacle.

Internal catheters function well for short periods, but are too likely to cause infections or other problems in the bladder or urinary tract to permit long-term use.

External catheters have been found to be useful where a slow, steady urine flow occurs. But many problems occur where the urine flow is irregular, which is the usual case. If the sheath is not tight, seepage is likely to occur with resulting embarrassing odors and clothing stains. A very tight sheath may cause pain during involuntary erections. Where there is a sudden large flow or "burst" of urine, the entire sheath may be forced off of the penis causing a spillage of a large quantity of urine.

The straps used with some devices to hold the sheath in a place are uncomfortable and likely to fail. Also, a sudden large urine flow exceeding the short-term capacity of the drain line is likely to back up, expand the sheath and leak out the top.

Thus, there is a continuing need for improved external catheters for males which overcome these problems.

SUMMARY OF THE INVENTION

An external catheter assembly for incontinent males having an improved sealing arrangement resistant to leakage. The assembly consists of three parts. An elastic, generally frusto-conical, sealing means is provided having a first reinforcing ring at the base. The seal fits over the penis with the seal ring at the base of the penis and the portion lying along the penis in elastic engagement therewith. A rubbery sheath (which may be loose or a close fit, as desired) fits over the length of the penis with a connection to a drain tube at the end of the penis and a sheath reinforcing ring adjacent the base of the penis and seal ring. A nether garment, preferably similar to conventional briefs, surrounds the lower torso with a frontal opening through which the penis is extended. A collar surrounds the opening and is fixedly secured to the briefs. The collar includes a pair circular channel means separated by a flange with the channel openings oriented away from the penis. The sheath and seal reinforcing rings are sufficiently elastic to permit them to be stretched slightly and each snapped into one of the collar channels, sealing them thereto.

As detailed below, forces from a sudden surge of urine do not cause leakage and cannot force the sheath off of the penis because of the orientation of the sealing means and the attachment to the nether garment.

BRIEF DESCRIPTION OF THE DRAWING

Details of the invention, and of a preferred embodiment thereof, will be further understood upon reference to the drawing, wherein.

DETAILED DESCRIPTION OF THE INVENTION

Figure 1:
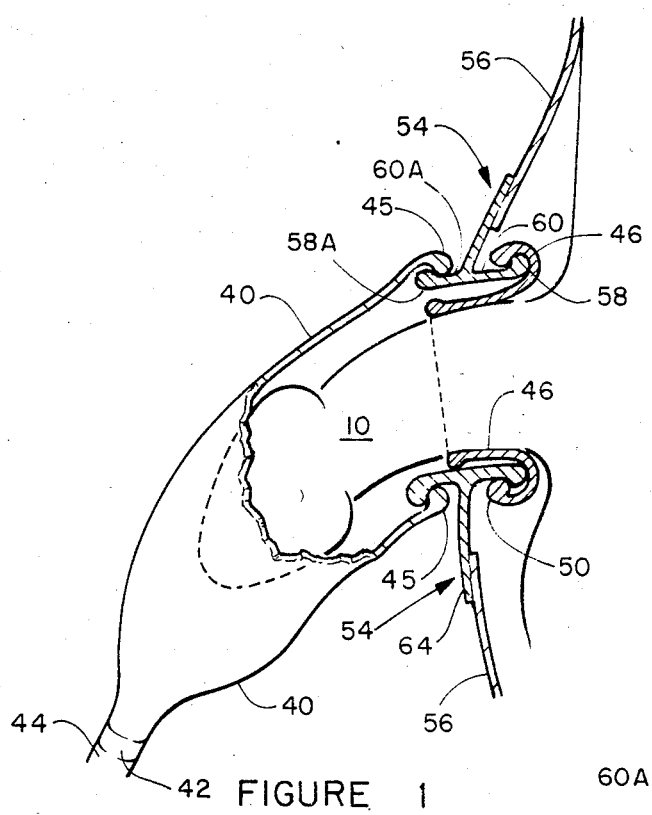
FIG. 1 is a schematic side view, partially cut-away, of the external catheter of this invention.

The improved external catheter of this invention is schematically shown in elevation in FIG. 1, with the assembly partially cut-away along the portion near the base of the penis for clarity. Here sheath 40 has a connection 42 to a drain line 44 at one end and a reinforcing ring 45 at the other. Sheath 40, connection 42 and drain line 44 may be molded in one piece, if desired. Drain line 44 leads to any suitable collection bag or the like. Sheath 40 need not be irritatingly tight to prevent leakage. Sheath 40 may be manufactured from any suitable rubbery or plastic urine-impervious material.

Figure 2:
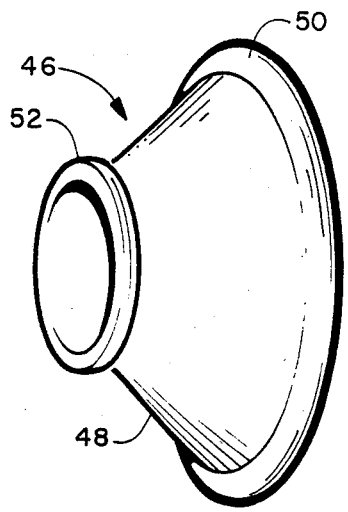
FIG. 2 is a perspective view of the seal means.

As seen in FIGS. 1 and 2, an internal seal means 46 is located within sheath 40. Seal means 46 includes a generally frusto-conical elastic wall or membrane 48 with a first, or seal, reinforcing ring 50 at the base and a second reinforcing ring 52 at the outer edge of the wall. While ring 52 is preferred in some cases, it may be eliminated where wall 48 has sufficient inherent edge strength to provide the necessary seal with the penis surface.

Figure 3:
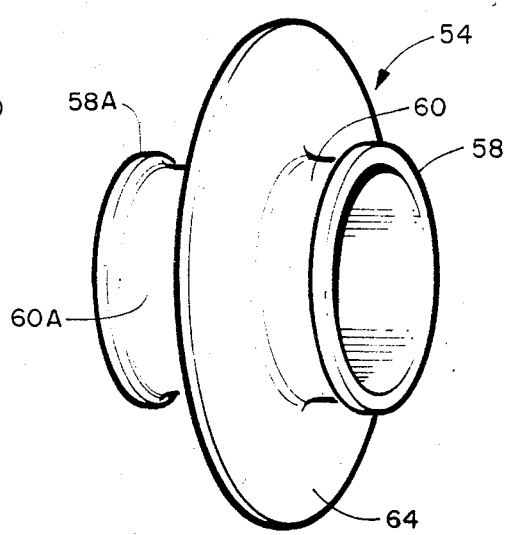
FIG. 3 is a perspective ivew of the collar means.

As seen in FIGS. 1 and 3, a ring-like collar 54 is fixedly secured in an opening in a nether garment 56. The penis 10 extends through collar 54 adjacent to sheath reinforcing ring 45 and seal reinforcing ring 50. Collar 54 has a generally channel-like cross section on either side of the flange 64, facing outward with inner and outer lips 58 and 58A respectfully and channel bases 60 and 60A respectfully. Rings 45 and 50 may be stretched slightly and snapped over lips 58 and 58A respectively, to be retained thereby against channel bases 60 and 60A.

Collar 54 may be formed from any suitable material. Polypropylene is preferred since it has a smooth, easily cleaned surface and is easily molded into the desired shape.

Figure 4:
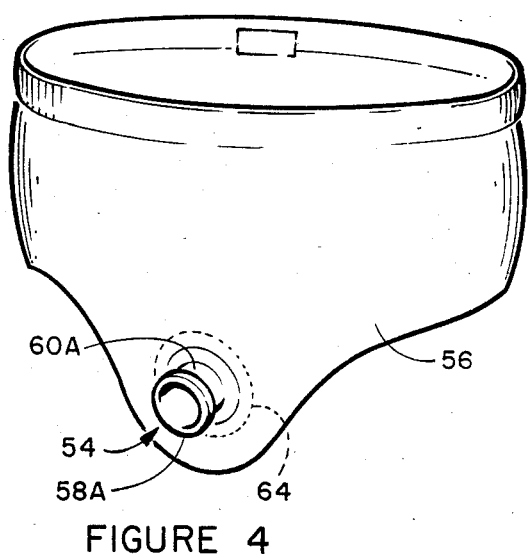
FIG. 4 is a perspective view of briefs with the collar means of FIG. 3 in place.

As seen in FIG. 4, collar 54 may be fastened into a hole in any suitable nether garment 56 by any conventional method, such as by sonic welding of flange 64 to the fabric or sewing through the fabric and flange. Typically garment 56 may be conventional men's briefs.

The catheter system may be made in several different diameters to accommodate penises of different diameters. In most cases, collar 54 may have an inside diameter of about 1.45 inches. The diameter of lips 58 and 58A then might be about 1.7 inches, to allow sheath and seal rings 45 and 50 having diameters of about 1.5 inches to be snapped thereover and to be held in place.

With the novel catheter assembly as seen in FIG. 1, a sudden flow of urine will tend to expand sheath 40 (which can be a loose fit and of easily expandable material if desired), the pressure will tend to press the wall 48 of inner seal 46 and ring 52 more tightly against the penis, preventing leakage. Even with a very great and sudden urine flow, sheath 40 will be held in place by collar 54 and garment 56.

While certain preferred dimensions, materials and arrangements were described in conjunction with the above description of a preferred embodiment, these may be varied, where suitable, with similar results. For example, sheath 40 may be formed from any suitable material and may be snug or loose, as desired.

Other modifications, variations and ramifications of this invention will occur to those skilled in the art upon reading this disclosure. Those are intended to be included within the scope of this invention, as defined in the appended claims.

I claim:

1. An external urine catheter system for incontinent males which comprises:

a nether garment means adapted to engage and surround the lower trunk of a user, said nether garment means having an aperture therein;

a ring-like annular collar means for insertion into said aperture, said ring-like collar means having inner and outer lip means with an annular flange means positioned between said lip means, said inner lip means oriented toward the body of a user, intermediate between each said lip means and said annular flange means is a channel base means forming inner and outer channel base means, said annular flange means is fixedly secured to said nether garment, a longitudinal centrally disposed axial bore means extends completely through said collar means for the insertion of a user's penis and an internal seal means, said internal seal means includes a hollow frusto-conical elastic membrane having a base at a larger inner end of said seal means and an outer edge portion means, said base having a first reinforcing ring means for overlapping the inner lip means of said collar means and into said inner channel base means, said outer edge portion means for engaging the user's penis in a sealing manner;

a flexible tubular sheath having at one end a connecting means and a drain tube and a reinforcing ring means at opposite end for overlapping said outer lip portion of said collar means and removably engaging said outer channel base means, said sheath having an intermediate section to enclose a user's penis.

2. The external catheter system according to claim 1 further including a second seal reinforcing ring at the outer edge of said generally frusto-conical membrane, said second seal ring adapted to elastically engage a penis extending through the seal.

3. The external catheter system according to claim 1 wherein said collar is fixedly fastened in conventional men's briefs.

4. The external catheter system according to claim 1 wherein said collar is formed from polypropylene and is fixedly secured to the edge of the hole in said nether garment by sonic welding.

5. The external catheter system according to claim 1 wherein said sheath, connection and drain tube are manufactured as a single integral unit.

6. The external catheter system according to claim 1 wherein the material of construction and the diameter of said sheath are selected to provide engagement with said penis.

7. The external catheter system according to claim 1 wherein the diameter of said sheath is selected to provide loose fit on said penis.

* * * * *